United States Patent
Cade et al.

(10) Patent No.: US 10,130,587 B2
(45) Date of Patent: Nov. 20, 2018

(54) HARD CAPSULES

(75) Inventors: Dominique Nicolas Cade, Colmar (FR); Takahisa Takubo, Kanagawa (JP)

(73) Assignee: Capsugel Belgium NV, Bomem (BE)

( * ) Notice: Subject to any disclaimer, the term of this patent is extended or adjusted under 35 U.S.C. 154(b) by 560 days.

(21) Appl. No.: 13/979,087

(22) PCT Filed: Jan. 10, 2012

(86) PCT No.: PCT/IB2012/000176
§ 371 (c)(1),
(2), (4) Date: Jul. 10, 2013

(87) PCT Pub. No.: WO2012/095746
PCT Pub. Date: Jul. 19, 2012

(65) Prior Publication Data
US 2013/0287842 A1    Oct. 31, 2013

Related U.S. Application Data

(60) Provisional application No. 61/431,496, filed on Jan. 11, 2011.

(51) Int. Cl.
*A61K 9/48* (2006.01)

(52) U.S. Cl.
CPC ................ *A61K 9/4816* (2013.01)

(58) Field of Classification Search
None
See application file for complete search history.

(56) References Cited

U.S. PATENT DOCUMENTS

| | | | |
|---|---|---|---|
| 3,784,390 A | | 1/1974 | Hijiya et al. |
| 4,004,977 A * | | 1/1977 | Kato et al. ............... 435/102 |
| 5,264,223 A | | 11/1993 | Yamamoto et al. |
| 5,756,123 A | | 5/1998 | Yamamoto et al. |
| 7,267,718 B2 * | | 9/2007 | Scott et al. ............ 106/205.01 |
| 2005/0249676 A1 * | | 11/2005 | Scott et al. .................... 424/46 |

FOREIGN PATENT DOCUMENTS

| | | |
|---|---|---|
| CA | 1037887 | 9/1978 |
| DE | 2504108 | 1/1976 |
| EP | 0 586 034 A2 | 3/1994 |
| EP | 1 072 633 A1 | 1/2001 |
| EP | 0 714 656 B1 | 2/2001 |
| EP | 1 157 691 A1 | 11/2001 |
| EP | 1 398 346 A1 | 3/2004 |
| EP | 1 117 736 B2 | 8/2008 |
| EP | 2 583 982 A1 | 4/2013 |
| FR | 2259905 | 8/1975 |
| GB | 1443918 | 7/1976 |
| JP | S48-21739 A | 3/1973 |
| JP | S50-105887 A | 8/1975 |
| JP | 05-65222 A | 3/1993 |
| JP | 2005-137935 A | 6/2005 |
| WO | WO 03/039522 A1 | 5/2003 |
| WO | WO 2005/105051 A1 | 11/2005 |
| WO | WO 2006/082842 A1 | 8/2006 |
| WO | WO 2009/050646 A2 | 4/2009 |
| WO | WO 2009/138920 A1 | 11/2009 |

OTHER PUBLICATIONS

European Patent Office Communication dated May 2, 2014, from related EPC Patent Application No. 12705407.0 (6 pages).
International Search Report dated Aug. 7, 2012, from related International Application No. PCT/IB2012/000176 (3 pages).
Written Opinion dated Aug. 7, 2012, from related International Application No. PCT/IB2012/000176 (5 pages).
Cadé et al., "Liquid Filling in Hard Gelatin Capsules—Preliminary Steps" *Bulletin Technique Gattefossé*, 89:15-19 (1996).
Millender, "Capsule Shell Composition and Manufacturing" in *Multiparticulate Oral Drug Delivery. Drugs and the Pharmaceutical Sciences*, vol. 65. New York, New York, USA: Marcel Dekker, Inc., 1994; pp. 357-383.
Morris "Quantitative determination of carbohydrates with Dreywood's anthrone reagent" *Science*, 107:254-255 (1948).
Notice of Reasons for Rejection dated May 12, 2015, from related Japanese Patent Application No. 2013-548905, with English-language translation (9 pages).

* cited by examiner

*Primary Examiner* — David Browe
(74) *Attorney, Agent, or Firm* — Klarquist Sparkman, LLP

(57) ABSTRACT

The present disclosure concerns embodiments of new hard pullulan capsule shells and capsules comprising (I) moisture, (II) a mono-, di-, and oligosaccharides free pullulan and (III) a setting system. Also provided are an aqueous composition and a dip-molding manufacturing method for the manufacture of such shells and capsules.

11 Claims, 2 Drawing Sheets

Figure 1:
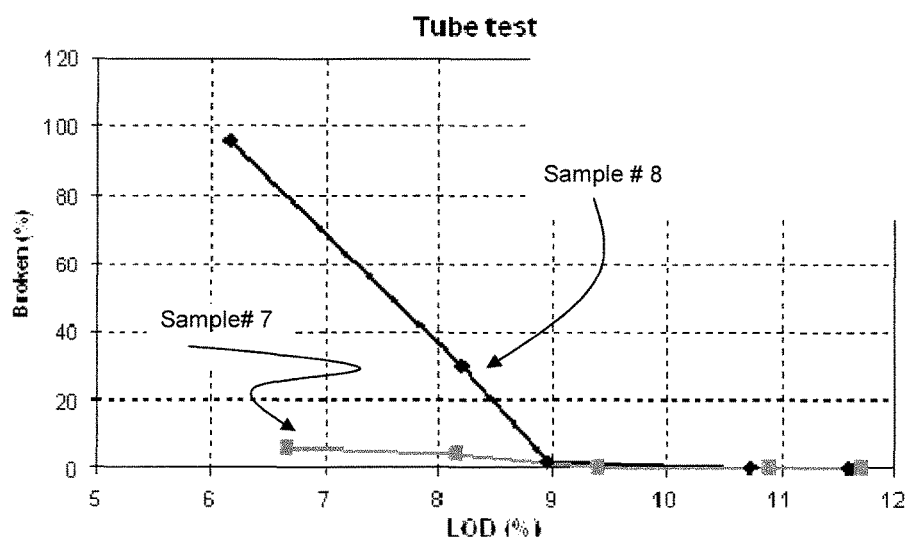

HARD CAPSULES

This application is national phase application based on International Application No. PCT/IB2012/000176, filed Jan. 10, 2012 which claims the benefit of U.S. Provisional Application No. 61/431,496, filed Jan. 11, 2011, all of which are incorporated herein by reference on their entirety.

FIELD OF THE INVENTION

The present invention relates to new hard capsule shells and capsules comprising pullulan, a dip-molding process for the manufacture thereof, aqueous dispersions for use in the dip-molding process and the use of a specific pullulan grade for the manufacture of hard capsule shells and capsules.

BACKGROUND OF THE INVENTION

Hard and soft capsules comprising pullulan are known.

WO2005105051 discloses a hard capsule comprising a conventional pullulan grade in an amount of 85% to 90% by weight, potassium chloride in an amount of 1.0% to 1.5% by weight, carrageenan in an amount of 0.1% to 0.4% by weight, one or more surfactants in an amount of 0.1% to 0.2% by weight and water in an amount of 10% to 15% by weight over the weight of the capsule. Thanks to the addition of a particularly selected setting system, WO2005105051 capsules are inter alia endowed with an improved chemical stability (e.g. no polymer cross-linking as with conventional gelatin). WO2005105051 does not disclose or suggest the use of any specific pullulan grade or the advantages following therefrom.

EP1072633 discloses compositions based on pullulan and a setting system for the use e.g. in manufacturing soft or hard capsules. EP1072633 stresses the importance of the addition of an appropriate setting system whereas no indication is given to select a specific pullulan grade or the advantages following therefrom.

EP1157691 discloses pullulan compositions for use e.g. in manufacturing soft or hard capsules with improved surface properties. The advantage is obtained by using a surfactant of pharmaceutical or food quality. EP1157691 does not disclose or suggest the use of any specific pullulan grade or the advantages following therefrom.

EP1398346 discloses the manufacturing of a high pullulan content shaped products (such as hard capsules) comprising α,α-threalose and a pullulan having an average molecular weight between 20,000 and 4,000,000 Dalton, preferably between 50,000 and 2,000,000 Dalton, in an amount of 30% or higher on a dry solid basis. The presence of α,α-threalose is praised as the key factor to impart the final products with properties such as stability to the change of humidity, transparency, gloss, and solubility in water. Although the use of PI-20, PF-10 and PF-20 pullulan grades is disclosed, no indication is given to select other specific and more advantageous pullulan grades.

JP5-65222-A describes a soft capsule, capable of stabilizing a readily oxidizable substance enclosed therein, exhibiting easy solubility, and being able to withstand a punching production method. The soft capsule is obtained by blending a capsule film substrate such as gelatin, agar, or carrageenan with pullulan. No indication is given to select a specific pullulan grade or the advantages following therefrom.

The hard capsule shells disclosed in the prior art present certain drawbacks, notably a non fully satisfactory shell mechanical strength (i.e. shell brittleness) at shell low LOD. Improving this property is a particularly desirable goal for pullulan hard capsule shells. Pullulan is in fact more sensitive than other materials (e.g. gelatin or HPMC) to low moisture conditions. This sensitivity impinges upon increased shell brittleness at low water content. Unsatisfactory brittleness means higher manufacturing losses, a poorer quality and global higher costs. On the other hand, reducing LOD of the shell might be desirable to encapsulate those active principles and natural or synthetic substances that are sensitive to water. A shell low LOD is also obtained when hard shells are filled with hygroscopic substances that make the shell moisture to migrate from the shell to the filling so as to simulate a further drying of the shell.

Accordingly, one object of the present invention is therefore the provision of pullulan hard capsule shells and capsules which overcome the drawbacks of the prior art. In particular, one object of the present invention is the provision of new pullulan hard shells and capsules that with respect to prior art pullulan hard capsule shells present improved characteristics in terms of shell mechanical properties especially at low shell LOD levels, and an equally good or improved shell dissolution profile, shell transparency, capsule surface static and gliding properties, absence of unpleasant smell, capsule compatibility with automatic high speed capsule filling equipment.

Another object of the invention is to provide a dip-molding manufacturing process that allows for the manufacture of the improved hard capsule shells as above, in an easy and cost-effective manner and that allows maintaining capsule dimension specificities during production.

SUMMARY OF THE INVENTION

The above and other objects are achieved by an aqueous composition for the manufacture of hard capsule shells characterized in that it comprises (i) an aqueous solvent, (ii) a mono-, di-, and oligosaccharides free pullulan and (iii) a setting system.

The above and other objects are also achieved by a hard capsule shell comprising (I) moisture, (II) a mono-, di-, and oligosaccharides free pullulan and (III) a setting system.

The above and other objects are also achieved by a hard capsule comprising a shell as defined above filled with one or more substances in solid, semi-solid and/or liquid form.

The above and other objects are also achieved by a dip-molding method for the manufacture of hard capsule shells as defined above, said process comprising the steps of:
(a) dipping pins into an aqueous composition as defined above
(b) withdrawing the dipping pins from the aqueous composition and
(c) drying the composition adhered on the dipping pins so as to obtain a shell;
wherein the steps (a) to (c) are performed in the order in which they are presented.

The above and other objects are also achieved by the use of a mono-, di-, and oligosaccharides free pullulan for the manufacture of hard capsule shells.

FIGURES

Figure 2:
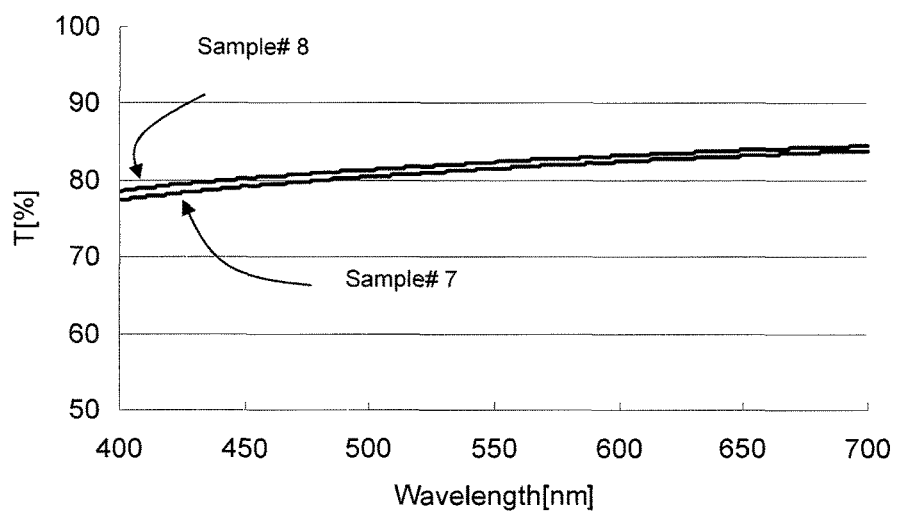
Figure 3:
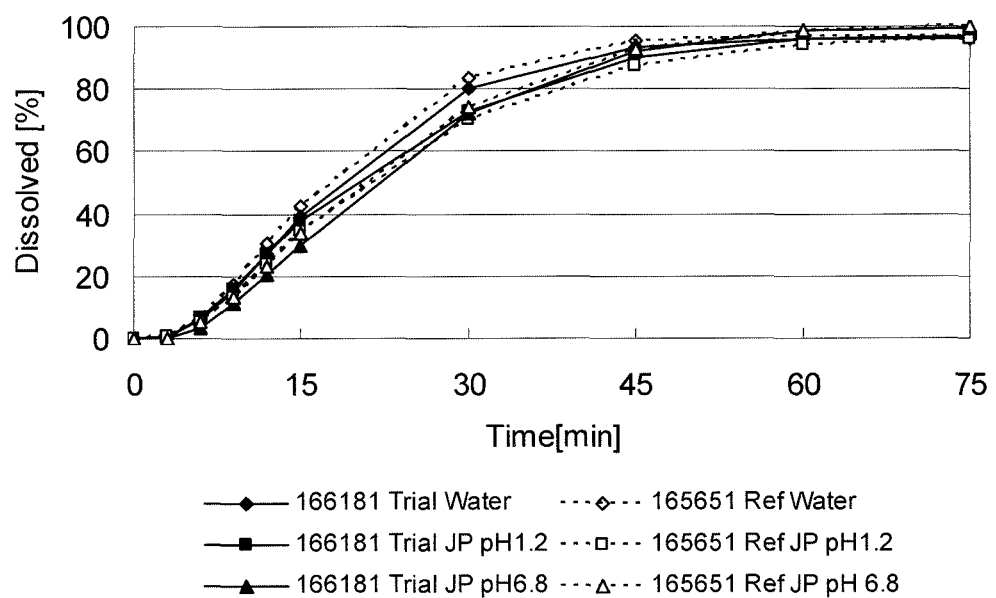

FIG. 1 is a graph representing shell mechanical properties for shells of the present disclosure ("Sample #7" of Example 4) and comparative conventional pullulan shells ("Sample #8" of Example 4) by means of the tube test after storage at different RH conditions, illustrating that the comparative conventional pullulan shells exhibit higher brittleness as compared to the shells of the present disclosure, wherein "Broken %" refers to the percentage of broken capsules and "LOD %" refers to loss-on-drying;

FIG. 2 is a graph representing shell transmittance measurements for shells of the inventions (Sample#7—see sample details in example 4) and (comparative) conventional pullulan shells (Sample#8—see sample details in example 4). Transmittance measured with spectrophotometer over the wavelength from 400 to 700 nm;

FIG. 3 is a graph representing shell dissolution properties for shells of the inventions (Sample#7—see sample details in example 4—identified by Lot#166181) and (comparative) conventional pullulan shells (Sample#8—see sample details in example 4—identified by Lot#165651). Shells were filled with APAP. Test conditions are disclosed below. Results in the graph are the average of the values obtained for 6 capsules.

DETAILED DESCRIPTION OF THE INVENTION

Below, any consideration and embodiment disclosed in connection with one aspect of the invention (e.g. the aqueous composition) must be understood to equally apply to the other aspects of the invention (e.g. hard capsule shells, hard capsules, the dip-molding process and uses) to the extent that it is technically possible.

In a first aspect, the present invention relates to an aqueous composition for the manufacture of hard capsule shells characterized in that it comprises (i) an aqueous solvent, (ii) a mono-, di-, and oligosaccharides free pullulan and (iii) a setting system.

In one embodiment, the aqueous composition of the invention has a total amount of solids typically comprised between about 10% and 55% by weight, preferably between about 15% and 40%, more preferably between 20% and 30% by weight over the total weight of the composition.

In one embodiment, the aqueous composition of the invention has a total amount of solids so that the viscosity of the aqueous composition at a temperature comprised between about 50° C. and 60° C. is comprised between about 500 cPs and 1500 cPs, preferably between about 800 cPs and 1000 cPs.

Unless otherwise indicated, the term "solids" includes at least all non aqueous ingredients added into the aqueous composition of the invention. Solids in particular comprise a mono- di, and oligosaccharide free pullulan and a setting system. Solids also comprise other optional ingredients typically used in hard capsule manufacturing such as plasticizers, surfactants, sequestring agents, pharmaceutically or food acceptable flavouring agents, pharmaceutically or food acceptable dyes and pharmaceutically or food acceptable colouring agents, if present.

Unless otherwise indicated, "aqueous solvent" preferably means water, more preferably deionised water. More preferably "aqueous solvent" consists of deionised water. In one embodiment, demineralised water is preferably demineralised water for pharmaceutical uses as defined under USP purified water in the USP-32.

Pullulan (CAS number 9057-02-7; chemical synonyms 1,4-1,6-α-D-Glucan, 1,6-α-linked maltotriose) is a polysaccharide polymer consisting of maltotriose units. Three glucose units in maltotriose are connected by an α-1,4 glycosidic bond, whereas consecutive maltotriose units are connected to each other by an α-1,6 glycosidic bond. Maltotetraose units consisting of four 1,4-linked glucose molecules also occur, probably randomly, but are rare (about 6%). There is also evidence for a rare occurrence of branching points where poly-maltotriosyl side-chains are attached to the main chain by a 1,3-glycosidic bond.

Pullulan is generally produced from starch by the fungus *Aureobasidium pullulans*. Pullulan has good film forming properties and a particularly low oxygen permeability. Its existence was reported for the first time in 1938. Hayashibara Company started the commercial production in 1976.

Unless otherwise indicated, pullulan of the present invention is a pullulan as defined above which is further characterized by being free of mono-, di-, and oligosaccharides. Pullulan can be made free of mono-, di-, and oligosaccharides either throughout a post-manufacturing process step (e.g. precipitation of the mono-, di-, and oligosaccharides from a sample of a commercial pullulan grade in ethanol) or from its very production, by choosing appropriate starch fermentation conditions. Mono-, di-, and oligosaccharides free pullulan for use in this invention has been purchased from Hayashibara Company, Okayama Japan.

In one embodiment, the pullulan of the present invention has preferably an average molecular weight comprised between about 100 KDa and 400 KDa, preferably between 150 KDa and 350 KDa, more preferably between 200 KDa and 330 KDa.

In one embodiment, the pullulan of the present invention has preferably a melt viscosity at about 60° C. between about 500 cPs and 1500 cPs, preferably between about 800 cPs and 1000 cPs.

In one embodiment, "mono-, di-, and oligosaccharide free pullulan" preferably means that the amount of mono-, di- and oligosaccharides in a pullulan sample is preferably lower than 2.5%, preferably lower or equal to 1%, preferably lower than or equal to 0.9%, more preferably lower than or equal to 0.7%, even more preferably lower than or equal to 0.6%, by weight over the total weight of the pullulan sample, on a dry solid basis. In one embodiment, "dry solid basis" preferably means that the content of mono-, di-, and oligosaccharides is measured in a sample of pullulan containing water in an amount comprised between about 0.5% and 2% by weight over the total weight of the sample.

Unless otherwise indicated, mono-, di-, and oligosaccharides of pullulan are measured as glucose units. Unless otherwise indicated, a pullulan monosaccharide is preferably a glucose monomer; a pullulan disaccharide is preferably a glucose dimer; a pullulan oligosaccharide preferably comprises between about 3 and 10 glucose monomers.

Mono-, di-, and oligosaccharides are the main pullulan impurities. Methods to calculate the % by weight of mono-, di-, and oligosaccharides (as glucose units) over the total weight of a pullulan sample are known to a skilled man. For example, reference can be made to the anthrone-sulfuric acid method disclosed in Morris D. L. (1948) "Quantitative determination of carbohydrates with Dreywood's anthrone reagent", Science 107: 254-255:

Equipment

Spectrophotometer capable of measuring absorbance at 620 nm

Procedure

Preparation of standard: Weigh accurately 0.2 g glucose, dissolve in water and make up to 1 l.

Measurement of mono-, di- and oligosaccharides

Weigh accurately 0.8 g sample and dissolve in water to make 100 ml (stock solution). Place 1 ml of the stock solution in a centrifuge tube. Add 0.1 ml saturated potassium chloride solution. Add 3 ml methanol and mix vigorously for 20 sec. Centrifuge at 11000 rpm for 10 minutes. Add 0.2 ml of the supernatant to 5 ml modified anthrone solution (0.2 g anthrone in 100 g 75% (v/v) sulfuric acid, freshly prepared). Add 0.2 ml of glucose standard solution and 0.2 ml water (blank control) to separate 5 ml portions of modified anthrone solution. Mix rapidly. Place samples in a 90° water bath and incubate for 15 min. Measure absorbance of the test solution at 620 nm. Calculate the percent of mono-, di- and oligosaccharides expressed as glucose (C) in the sample:

$C(\%)=[(At-Ab) \times 0.41 \times G \times 100]/(As-Ab) \times W$ where

At is absorbance of the test solution
Ab is absorbance of the water blank
As is absorbance of the standard solution
G is weight of the glucose (g)
W is weight of the sample (g)

Without wanting to be bound by any theory, it is believed that the use of a mono-, di-, and oligosaccharides free pullulan plays an important role in achieving the improved properties of the shells and capsules of the invention, notably in terms of improved shell mechanical properties especially at low shell LOD levels. A commercially available pullulan grade is for example Pullulan PI-20 (tradename from Hayashibara) where "P" stands for "pullulan", "I" for "de ionized" and the FIG. 20 designates the average molecular weight of about 200 kDa. Another commercially available de ionized pullulan grade is PI-10 (tradename from Hayashibara) having average molecular weight of about 100 kDa. Food grade pullulans are also commercially available. For example, Hayashibara commercializes PF-10 and PF-20 grades (both tradename) having average molecular weights of about 100 kDa and 200 KDa, respectively. Typically, a sample of a commercially available pullulan grade (such as grade PI-20) contains between 7% and 10% by weight of mono-, di- and oligosaccharides over the total weight of pullulan sample, on a dry basis. As shown in the examples of the present application, these levels of mono-, di- and oligosaccharides do not allow obtaining the advantageous properties shown by the hard capsule shells and capsules of the invention.

In one embodiment, the aqueous composition of the invention contains a mono-, di-, and oligosaccharides free pullulan as defined above in an amount suitable to obtain a hard capsule shell as defined below containing between about 65% and about 99% by weight, preferably between about 65% and about 98% by weight, more preferably between about 70% and about 97% by weight, more preferably between about 85% and about 96% by weight of such pullulan over the weight of the shell. Hard capsule shells meeting the above weight % can typically be manufactured via dip-molding by using aqueous compositions comprising between about 15% and 40%, preferably between about 15% and 30%, even more preferably between about 18% and 25% by weight of such pullulan over the total weight of the aqueous composition.

In one embodiment, the mono-, di-, and oligosaccharides free pullulan as defined above represents more than 50%, preferably more than 75%, even more preferably 100% by weight over the weight of the total pullulan present in the aqueous composition, the shells and capsules of the present invention.

In one embodiment, the mono-, di-, and oligosaccharides free pullulan is produced from a generic source of starch, preferably the starch is corn or tapioca starch. In one embodiment, the mono-, di-, and oligosaccharides free pullulan is produced from corn starch. In one embodiment, the mono-, di-, and oligosaccharides free pullulan is produced from tapioca starch.

In one embodiment, the aqueous composition of the invention optionally comprises additional film-forming polymers typically used in the manufacture of hard capsule shells. Typically, such additional film-forming polymers are selected from the group consisting of: gelatin, polyvinyl alcohol, starch, starch derivatives (for example hydroxyethylated and hydroxypropylated starches), cellulose, celluloses derivatives (for example HEC, HMC or HPMC such as HPMC USP30-NF25 grade 2208, 2906 or, preferably, 2910) and mixtures thereof. Preferably, additional film-forming polymers are selected from the group consisting of: gelatin, HPMC, starch derivatives and mixture thereof. In one embodiment, the aqueous composition of the invention optionally comprises gelatin. In one embodiment, the aqueous composition of the invention optionally comprises HPMC. In one embodiment, the aqueous composition of the invention optionally comprises starch derivatives.

In one embodiment, the mono-, di-, and oligosaccharides free pullulan as defined above represents more than 50%, preferably more than 75%, even more preferably 100% by weight over the weight of all the film-forming polymers typically used in the manufacture of hard capsule shells and optionally present in the aqueous composition, the shells and capsules of the present invention. Preferably, such film-forming polymers are as defined above. The embodiment wherein the pullulan of the invention represents 100% by weight of all the film-forming polymers present in the aqueous composition preferably means that the aqueous composition of the invention contains traces of, or more preferably does not contain any one of the following polymers: gelatin, polyvinyl alcohol, starch, starch derivatives (for example hydroxyethylated and hydroxypropylated starches), cellulose, celluloses derivatives (for example HEC, HMC or HPMC such as HPMC USP30-NF25 grade 2208, 2906 or preferably 2910) and mixtures thereof.

Setting systems are conventionally relied upon in the manufacture of hard capsule shells by non-thermogelling dip-molding processes to confer an appropriate setting ability with cooling to film-forming polymers (like pullulan, HPMC or starch derivatives) that in these conditions have per se poor gelling properties. The setting system makes the aqueous composition to set on the dipped pins, thus assuring a uniform capsule shell thickness.

A huge patent literature provides guidance as to select the most effective setting system(s) depending on the film-forming polymers to be used in the capsule shell manufacturing. Reference can be made for example to U.S. Pat. No. 5,264,223 and EP714656 (discussing HPMC capsules), EP1117736 (discussing starch derivatives capsules); WO2005105051 and EP1072633 (discussing pullulan capsules).

In one embodiment, the setting system of the invention comprises one or more gelling agents. In one embodiment, the setting system of the invention comprises one or more gelling agents and one or more gelling aids (also known as co-gelling agents).

In one embodiment, the one or more gelling agents are selected from the group consisting of alginates, agar gum, guar gum, locust bean gum (carob), carrageenan (preferably kappa and/or iota), tara gum, arabic gum, ghatti gum, khaya grandifolia gum, tragacanth gum, karaya gum, pectin, arabian (araban), xanthan, gellan gum, starch, konjac mannan, galactomannan, funoran, acetan, welan, rhamsan, furcelleran, succinoglycan, scleroglycan, schizophyllan, tamarind gum, curdlan, dextran and mixtures thereof. Preferably, the one or more gelling agents are selected from the group consisting of carrageenans (preferably kappa and/or iota, more preferably kappa-carrageenans), gellan gum and mixtures thereof. In one embodiment, the one or more gelling agents comprise, preferably consist of carrageenans (preferably kappa and/or iota, more preferably kappa-carrageenans). In one embodiment, the one or more gelling agents comprise, preferably consist of gellan gum. In one embodiment, the one or more gelling agents comprise a combination of two or more of the agents listed above. In one embodiment, the one or more gelling agents comprise, preferably consist of a combination of xanthan and locust bean gum. In one embodiment, the one or more gelling agents comprise, preferably consist of a combination of xanthan with konjac mannan.

In one embodiment, the one or more gelling aids (also known as co-gelling agents) are cations. In one embodiment, the one or more gelling aids are selected from the group consisting of: $K^+$, $Li^+$, $Na^+$, $NH_4^+$, $Ca^{2+}$, $Mg^{2+}$ and mixtures thereof. Preferably, the one or more gelling aids are selected from the group consisting of: $K^+$, $NH_4^+$, $Ca^{2+}$ and mixtures thereof. The cations can be added to the setting system in the form of a pharmaceutically or food acceptable water soluble salt (e.g. chloride, citrate or phosphate).

In one embodiment, the setting system of the invention comprises, preferably consists of:
  one or more gelling agents selected from the group consisting of carrageenans (preferably kappa and/or iota, more preferably at least kappa-carrageenans), gellan and mixtures thereof; and
  one or more pharmaceutically or food acceptable water soluble salts of $K^+$, $NH_4^+$, $Ca^{2+}$ and mixtures thereof.

In one embodiment, the aqueous composition of the invention contains one or more gelling agents as defined above in an amount suitable to obtain a hard capsule shell as defined below containing between about 0.01 and 3.0%, by weight, preferably between about 0.03 and 1.0%, by weight, preferably between about 0.1% and 0.5% by weight of such gelling agent(s) over the weight of the shell. Exemplary suitable gelling agents' amounts are readily available to a skilled person in the field of hard capsules manufacturing. For example it is commonly accepted that hard capsule shells containing a "target" amount of gelling agents falling within the ranges identified above can be obtained via a dip-molding process by using aqueous compositions containing about ¼ (i.e. 25%) of that target amount (expressed as % by weight over the weight of the composition).

In one embodiment, the aqueous composition of the invention contains one or more gelling aids as defined above in an amount suitable to obtain a hard capsule shell as defined below containing about less than 3%, preferably about less than 2.0%, more preferably between about 0.5% to 2.0%, even more preferably between about 1.0% and 2.0% by weight of such one or more gelling aids over the weight of the shell. In case the gelling aids are cations, the above ranges are expressed as weight of the pharmaceutically or food acceptable water soluble salts containing the cation(s) over the weight of the shell. Exemplary suitable gelling aids' amounts are readily available to a skilled person in the field of hard capsules manufacturing. For example, it is commonly accepted that when water is about 75% by weight over the weight of the aqueous composition, hard capsule shells containing a "target" amount of gelling aids can be obtained via a dip-molding process by using aqueous compositions containing about ¼ (i.e. 25%) of that target amount (expressed as % by weight over the weight of the composition).

In one embodiment, the aqueous composition of the invention optionally comprises one or more pharmaceutically or food acceptable dyes and/or colouring agents.

Said dyes and/or colouring agents may be selected from the group consisting of azo-, quinophthalone-, triphenylmethane-, xanthene- or indigoid dyes, iron oxides or hydroxides, titanium dioxide or natural dyes and mixtures thereof. Further examples are patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, clorophyllin, canthaxanthin, caramel, betanin and Candurin® pearlescent pigments. Candurin® is manufactured and marketed by Merck KGaA, Darmstadt, Germany and consist of titanium dioxide and/or iron oxide—approved food and pharmaceutical colorants in many countries—and potassium aluminium silicate as color carrier. The latter is a natural, also widely approved, silicate also known under the name of 'mica'.

In one embodiment, the aqueous composition of the invention contains one or more pharmaceutically or food acceptable dyes and/or colouring agents as defined above in an amount suitable to obtain a hard capsule shell as defined below containing between about 0% and 5.0% by weight, preferably between about 0% and 4.0% by weight, more preferably between about 0% and 2.0% by weight of such one or more pharmaceutically or food acceptable dyes and/or colouring agents over the weight of the shell. Hard capsule shells meeting the above weight % can typically be manufactured via dip-molding by using aqueous compositions comprising between about 0% and 0.8% by weight, preferably between about 0% and 0.6% by weight, more preferably between about 0% and 0.4% by weight of over the total weight of the aqueous composition. For example, it is commonly accepted that when water is about 75% by weight over the weight of the aqueous composition, hard capsule shells containing a "target" amount of dyes and/or colouring agents can be obtained via a dip-molding process by using aqueous compositions containing about ¼ (i.e. 25%) of that target amount (expressed as % by weight over the weight of the composition).

In one embodiment, the aqueous composition of the invention optionally comprises one or more pharmaceutically or food acceptable sequestering agents. Preferably, said one or more sequestring agents are selected from the group consisting of EDTA acid, acetic acid, boric acid, citric acid, edetic acid, gluconic acid, lactic acid, phosphoric acid, tartaric acid, or salts thereof, methaphosphates, dihydroxyethylglycine, lecithin or beta cyclodextrin and combinations thereof. Especially preferred are ethylenediaminetetraacetic acid, citric acid or any pharmaceutically or food acceptable salt thereof.

In one embodiment, the aqueous composition of the invention contains one or more sequestering agents as defined above in an amount suitable to obtain a hard capsule shell as defined below containing between about 0% and 2.0% by weight of such sequestering agents over the weight of the shell. Exemplary suitable sequestering agents' amounts are readily available to a skilled person in the field of hard capsules manufacturing. For example, it is commonly accepted that when water is about 75% by weight over the weight of the aqueous composition, hard capsule shells containing a "target" amount of sequestering agents can be obtained via a dip-molding process by using aqueous compositions containing about ¼ (i.e. 25%) of that target amount (expressed as % by weight over the weight of the composition).

In one embodiment, the aqueous composition of the invention optionally comprises one or more pharmaceutically or food acceptable plasticisers.

In one embodiment, the one or more plasticizers are selected in the group of plasticizers typically used in the manufacture of hard capsule shells and in particular in the group consisting of: phtalique esters (e.g. dimethyl-, diethyl-, dibutyl-, diisopropyl- and dioctyl-phtalate); citric esters (e.g. triethyl-, tributyl-, acetyltriethyl- and acetyltributyl-citrate); phosphoric esters (e.g. triethyl-, tricresyl, triphenyl-phosphate); oils (e.g. purified mineral oils, ricin oil, corn oil, cotton oil); butyl stearate; dibutyl sebacate; dibutyl tartrate; diisobutyl adipate, glycerol monostearate; glycerol triacetate; tributyrin; oleic acid; stearic acid; cetylic acid; myristic acid; propylene glycol; glycerol; PEG 4000, PEG 6000, and mixtures thereof.

In one embodiment, and to avoid excessive shell softness, the aqueous composition of the invention contains one or more plasticizers as defined above in an amount suitable to obtain a hard capsule shell as defined below containing between about 0% and 10% by weight of such plasticizer(s) over the weight of the shell. Hard capsule shells meeting the above weight % can typically be manufactured via dip-molding by using aqueous compositions comprising less than about 2.0%, more preferably between 0% and 1.0% by weight over the total weight of the aqueous composition.

In one embodiment, the aqueous composition of the invention optionally comprises one or more pharmaceutically or food acceptable sweeteners and/or flavouring agents.

In one embodiment, the aqueous composition of the invention contains one or more pharmaceutically or food acceptable sweeteners and/or flavouring agents as defined above in an amount suitable to obtain a hard capsule shell as defined below containing between about 0% and 1.0% by weight of such sweeteners and/or flavouring agents over the weight of the shell. Exemplary suitable sweeteners and/or flavouring agents' amounts are readily available to a skilled person in the field of hard capsules manufacturing. For example it is commonly accepted that hard capsule shells containing a "target" amount of sweeteners and/or flavouring agents falling within the ranges identified above can be obtained via a dip-molding process by using aqueous compositions containing about ¼ (i.e. 25%) of that target amount (expressed as % by weight over the weight of the composition).

In one embodiment, the aqueous composition of the invention optionally comprises one or more pharmaceutically or food acceptable surfactants. Without wanting to be bound by any theory, it is believed that the surfactant contributes to the final hard capsule shell surface properties in such a way that the capsule works well on the conventional automatic high speed capsule filling equipment. Further guidance on possible embodiments for the surfactant and the advantages of including a surfactant in the aqueous composition of the invention can be found in WO2005/105051 filed by the present Applicant.

In one embodiment, the one or more pharmaceutically or food acceptable surfactants are selected from the group consisting of: sodium lauryl sulphate (SLS), dioctyl sodium sulfosuccinate (DSS), benzalkonium chloride, benzethonium chloride, cetrimide (trimethyltetradecylammonium bromide), fatty acid sugar esters for example like sorbitol esters (SE) and/or sucrose monolaurate (SML), glyceryl monooleate, polyoxyethylene sorbitan fatty acid esters, polyvinyl alcohol, dimethylpolysiloxan, sorbitan esters or lecithin. In one preferred embodiment, the one or more pharmaceutically or food acceptable surfactants comprise, more preferably consist of a mixture of SE and SML.

In one embodiment, the aqueous composition of the invention contains one or more pharmaceutically or food acceptable surfactants as defined above in an amount suitable to obtain a hard capsule shell as defined below containing between about 0% and 0.5% by weight of such surfactant(s) over the weight of the shell. Exemplary suitable sweeteners and/or flavouring surfactants' amounts are readily available to a skilled person in the field of hard capsules manufacturing. For example, it is commonly accepted that when water is about 75% by weight over the weight of the aqueous composition, hard capsule shells containing a "target" amount of surfactants can be obtained via a dip-molding process by using aqueous compositions containing about ¼ (i.e. 25%) of that target amount (expressed as % by weight over the weight of the composition).

In one embodiment, the aqueous composition of the invention consists of (i) an aqueous solvent as defined above, (ii) a mono-, di-, and oligosaccharides free pullulan as defined above (iii) a setting system as defined above and optionally, one or more of the following ingredients: one or more pharmaceutically or food acceptable dyes and/or colouring agents, one or more pharmaceutically or food acceptable sequestering agents, one or more pharmaceutically or food acceptable plasticisers, pharmaceutically or food acceptable sweeteners and/or flavouring agents and one or more pharmaceutically or food acceptable surfactants, all as defined above.

In one embodiment, the aqueous composition of the invention consists of (i) an aqueous solvent as defined above, (ii) a mono-, di-, and oligosaccharides free pullulan as defined above (iii) a setting system as defined above, one or more pharmaceutically or food acceptable surfactants as defined above and optionally, one or more of the following ingredients: one or more pharmaceutically or food acceptable dyes and/or colouring agents, one or more pharmaceutically or food acceptable sequestering agents, and one or more pharmaceutically or food acceptable plasticisers, pharmaceutically or food acceptable sweeteners and/or flavouring agents, all as defined above.

In a further aspect, the present invention relates to a hard capsule shell comprising (I) moisture, (II) a mono-, di-, and oligosaccharides free pullulan and (III) a setting system.

Unless otherwise indicated, in the present invention hard capsules have the same shape of commercially available, conventional hard capsules intended for oral administration to a human or animal being. The hard capsules of the invention can be manufactured by using a non-thermogelling dip molding process and equipment conventionally used for the manufacture of hard gelatin capsule shells. As it is disclosed in greater detail below, in the manufacturing process, pin molds (usually kept at about 25° C., i.e. room T) are dipped into an aqueous composition containing one or more film-forming polymers, as well as all the optional ingredients (e.g. setting system(s), plasticizer(s), colouring agent(s) etc) and subsequently withdrawn. The aqueous composition is typically kept at T generally comprised between 50° and 70° C. The film formed on pins surface is then dried, stripped off the pins and cut to a desired length. Thus, capsules caps and bodies are obtained. Normally, caps and bodies have a side wall, an open end and a closed end. The length of the side wall of each of said parts is generally greater than the capsule diameter. The capsule caps and bodies are telescopically joined together so as to make their side walls partially overlap and obtain a hard capsule shell. "Partially overlap" also encompasses an embodiment wherein the side walls of caps and bodies have substantially the same length so that, when a cap and a body are telescopically joined, the side wall of said cap encases the entire side wall of said body. Unless otherwise indicated, "capsule" refers to filled capsule shells whereas "shell" specifically refers to an empty capsule. Since the hard capsule shells of the invention can be filled with substances in liquid form, it is intended that if desired the hard capsules of the invention may be sealed or banded according to conventional techniques. Also, the hard capsule shells of the invention can be manufactures so to have a specific capsule shell design that provides with certain advantages as the possibility to pre-lock empty caps and bodies and complete the filling step in a different location/time. An example of advantageous designs suitable to be implemented in the hard capsule shells of the present invention can be found in WO2009/138920 (specifically when capsule filling is a liquid substance) or WO2009/050646.

Exemplary and preferred amounts of pullulan, setting system, dyes and/or colouring agents, sequestring agents, plasticizers, sweeteners and/or flavouring agents and surfactants in the shell of the invention are indicated above in the context of the aqueous composition.

Unless otherwise indicated, when discussing about shells and capsules of the invention, moisture and water are terms that can be used interchangeably.

The hard capsule shells of the invention typical comprise between 2% and 20%, preferably between about 5% and 15% by weight of moisture over the total weight of the shell.

Typically, a capsule of the invention is dried to an LOD comprised between about 10% and 15% can be considered acceptable for a capsule shell of the invention. However, LOD can be brought to lower % by e.g. further drying, capsule shell storage at low RH or following capsule shell filling with hygroscopic substances.

In one embodiment, the hard capsule shell of the invention consists of (I) moisture as defined above, (II) a mono-, di-, and oligosaccharides free pullulan as defined above (III) a setting system as defined above and optionally, one or more of the following ingredients: one or more pharmaceutically or food acceptable dyes and/or colouring agents, one or more pharmaceutically or food acceptable sequestering agents, one or more pharmaceutically or food acceptable plasticisers, pharmaceutically or food acceptable sweeteners and/or flavouring agents and one or more pharmaceutically or food acceptable surfactants, all as defined above. The presence of one or more pharmaceutically or food acceptable surfactants is preferred.

In one embodiment, the shells of the inventions may be externally coated with a suitable coating agent like cellulose acetate phthalate, polyvinyl acetate phthalate, methacrylic acid gelatins, hypromellose phthalate, hydroxypropylmethyl cellulose phthalate, hydroxyalkyl methyl cellulose phthalates, hydroxypropyl methylcellulose acetate succinate or mixtures thereof to provide e.g. enteric properties.

In one embodiment, the hard capsule shell of the invention is a shell obtainable using the aqueous composition of the invention as disclosed above. In one embodiment, the hard capsule shell of the invention is a shell obtainable using the aqueous composition of the invention as disclosed above and a dip-molding process of the invention as disclosed below.

In one embodiment, the hard capsule shell of the invention has a shell thickness (after drying till a shell LOD of lower than about 10%) lower than about 250 µm, preferably lower than about 150 µm, more preferably greater than about 70 µm, even more preferably between about 70 and 150 µm, even more preferably of about 100 µm. These shell thickness values cannot be obtained with non dip-molding manufacturing methods (e.g. injection molding) that typically give thicker shells of about 300 to 500 µm.

With respect to currently commercially available pullulan capsule shells (e.g. NPcaps® from Capsugel, France) the shells of the invention present improved characteristics in terms of shell mechanical properties especially at low shell LOD levels, and an equally good or improved shell dissolution profile, shell transparency, capsule surface static and gliding properties, absence of unpleasant smell, capsule compatibility with automatic high speed capsule filling equipment.

In one embodiment, low shell LOD levels preferably mean a shell LOD lower than about 9%, preferably lower than about 8%, more preferably comprised between about 7 and 8%. This LOD value is commonly adopted when filling shells with moisture sensitive or hygroscopic materials so that a lower shell brittleness at these value represent a significant advantage.

In one embodiment, shell mechanical properties at a specific shell LOD are tested according to the so-called "tube test". This test is well known to skilled men working in the field of hard capsules and one procedure for its performance is also disclosed in the literature (D. Cadé and N. Madit, "Liquid Filling in Hard Gelatin Capsules—Preliminary Steps", Bulletin Technique Gattefossé, 1996). During the tests, the % of broken capsule shells in a sample of several tens of shells is evaluated by varying the shell LOD: the lower the %, the lower the shell brittleness, the better the shell mechanical properties. As shown in the examples of this application, the capsule shells of the present invention showed a statistically reduced brittleness with respect to conventional pullulan capsules at shell LOD levels lower than about 10%, and notably at shell LOD levels comprised between about 7 and 8%.

In one embodiment, shell dissolution profile is tested by filling a sample of 6 hard capsule shells with acetaminophen, and verifying if one or more of the filled capsules in said batch release less than about 80% of the filled acetaminophen at 45 minutes in simulated gastric fluid (pepsin) after 6 months at storage conditions of 40° C. and 75% RH. Acetaminophen dissolution is evaluated in accordance with, and using equipment and method conditions disclosed in USP-32 for Acetaminophen. Such "Dissolution test", using an immediate release reference (i.e. acetaminophen), indicates changes in the capsule dissolution rate due to an inappropriate dissolution properties of the pullulan used for shell manufacture. In one embodiment, the method to test dissolution properties is performed as disclosed in D. Cadé and N. Madit, "Liquid Filling in Hard Gelatin Capsules—Preliminary Steps", Bulletin Technique Gattefossé, 1996.

In one embodiment, shell transmittance is tested according to the following procedure: cut a 1 $cm^2$ flat film sample from a capsule (size#2, natural transparent body), then measure its transmittance at 25° C. by using SHIMADSU UV1600PC spectrophotometer from 400 nm to 700 nm with 2 nm pitches of continuous scanning.

In one embodiment, shell static and glide properties are tested according to the methods disclosed in WO03/039522 ("Surface coated capsules"), Examples 2 and 1, respectively.

In one embodiment, shell smell is tested according to the following procedure: approximately 200 capsules are put in a 200 mL flask then plugged. Comparative capsules are put in another flask and plugged as well. Flasks are put in an oven at 40° C. for about 1 hour. Then panellists compare smell strength and rank it according to a scale comprising five smell strength levels ranging from 1 (lowest smell) to 5 (strongest smell).

In one embodiment, capsule compatibility with automatic high speed capsule filling equipment is tested according to the following procedure: in capsule filling machine (CFM), a vacuum pressure of about 20 cm Hg is applied to separate pre-locked bodies and caps in a batch of 1500 capsules. If all capsules can be separated, the test is re-run with a pressure of about 10 cm Hg. The number of capsules that cannot be separated at this step is recorded. Other parameters that are monitored are the number of capsules that incur cracking or deforming during separation. The highest the number of capsules that separate without defects, the higher the compatibility with the CFM machine.

In a further aspect, the present invention relates to a hard capsule comprising a shell as defined above filled with one or more substances in solid, semi-solid and/or liquid form.

In one embodiment, the one or more substances to be filled into the shells of the invention are substances that are sensitive to moisture or substances that are hygroscopic.

Unless otherwise indicated, substances that are sensitive to moisture preferably means substances that undergo any known chemical degradation following the contact with even minor amounts of water such as moisture content typical of hard gelatin capsules (for example, shell LOD comprised between 12% and 25%).

In one embodiment, preferred substances to be filled into the shells of the invention are selected from the group consisting of: placenta powder, aloe extract powder, pollen, activated carbon, glucosamine, carnitine, alfa-lipoic acid, royal jelly, propolis extract, garlic, seaweed extract, mineral salts, sesame extract, coenzyme, chitin, chitosan, chondroitin, glutathione, asteroid extract, soybean powder, lecithin, tea or herb powders, corn silk powder, *lactobacillus*, berry, wheat albumin, arginine, angleworm powder, ginger powder, champignon powders, kiwi extract, carrot extract, hyaluronic acid, grape-seed extract, collagen extract, lycopene, turmeric extract, lutein, catechin, plant extracts, nucleic acid, sugars, *chlorella*, vitamin, astaxanthin, yeast, shark extract, shellfish extract, other antioxidation compounds, and mixtures thereof.

In one embodiment, the hard capsules of the invention can be made tamper-proof by using appropriate techniques to make the joint between capsule caps and bodies permanent. Typically, sealing or banding techniques can be used where these techniques are well-known to any skilled person in the field of hard capsules. In this connection, it is conventional practice to perform banding and/or sealing using polymer solutions in water/ethanol or water/isopropanol solutions. Traces of such non water solvents thus can be found if an elemental analysis is performed on a sealed or banded capsule of the invention without making a distinction between ingredients that are part of the shell and ingredients that are part of the band or sealing subsequently applied.

In a further aspect, the present invention relates to a dip-molding method for the manufacture of hard capsule shells as defined above, said process comprising the steps of:
(a) dipping pins into an aqueous composition as defined above
(b) withdrawing the dipping pins from the aqueous composition and
(c) drying the composition adhered on the dipping pins so as to obtain a shell;
wherein the steps (a) to (c) are performed in the order in which they are presented.

Dip-molding processes for the manufacture of hard capsules using cooled pins and a solution of one or more film-forming polymers and optionally one or more gelling agents (e.g. carrageenans) and/or co-gelling agents (e.g. inorganic cations) is known since decades. For patent review disclosing this process one can see e.g. U.S. Pat. No. 5,264,223, U.S. Pat. No. 5,756,123 and U.S. Pat. No. 5,756,123 (all relating to HPMC capsule shells and entailing the use of setting systems).

In one embodiment, the method of the present invention comprises before step (a), a step of providing an aqueous composition as defined above.

In one embodiment, the method of the present invention comprises before step (a) but after the step of providing an aqueous composition as defined above, a further step of defoaming the aqueous composition provided.

In one embodiment, the method of the present invention comprises between steps (b) and (c), a further step of turning pins from a "top-down" dipping position (position of step (a)) to a "top-up" drying position (position in step (c)). In this additional step the pins are rotated about a horizontal axis of about 180° with respect to the dipping position of step (a).

In one embodiment, the pins in step (a) are kept at a pin dipping temperature which is preferably comprised between about 20° C. and 30° C., more preferably comprised between about 20° C. and 25° C.

In one embodiment, the aqueous composition in step (a) are kept at an aqueous composition dipping temperature which is preferably comprised between about 45° C. and 65° C., more preferably between about 50° C. and 65° C.

In one embodiment, step (c) of drying is performed according to conventional drying techniques typically applied in the field of hard capsules and by using conventional equipment known to the skilled person for this purpose. In one embodiment, step (c) of drying can be performed according to any technique commonly known for this purpose, for example by placing the pins in conventional ovens.

The method of the presence invention allows maintaining capsule dimension during production.

In one embodiment, maintenance of capsule dimension is tested according to the following in-line procedure: during manufacturing, an operator takes a sample of a predefined number of capsules and measures capsule bodies and caps weight as well as side and top wall thickness.

In a further aspect, the present invention relates to the use of a mono-, di-, and oligosaccharides free pullulan for the manufacture of hard capsule shells.

Further embodiments and advantages of the present invention will become apparent to a skilled reader in light of the examples provided below. Unless otherwise specified, all parts and percentages are by weight. Composition viscosities were determined by Brookfield viscometer.

Example 1

Hard capsule shell manufacturing—Samples 1-3 were prepared according to the following general procedure. Pullulan powder (amount to have a 22.5% by weight over the weight of the final aqueous composition—see below for pullulan grade details) is mixed with a gelling agent (see below for setting system definition and relative amount in each sample). To 5 kg of deionized water under stirring at room temperature a gelling aid is added (see below for gelling aid definition and relative amount in each sample), followed by addition of the above mixture. The powder addition and stirring speeds were very high in order to avoid the forming of lumps. The solution is heated up to 70° C. under stirring to totally dissolve the gelling agent and pullulan. It is possible to dissolve the components directly at 70° C., but the tendency of pullulan to lump is much higher. The pullulan solution thus prepared is defoamed under slow stirring and then poured into a dipping dish of a pilot machine of conventional hard gelatin capsule production equipment. Process conditions: as for standard NPcaps® capsules manufacturing, i.e. dish temperature 60° C.; mold pin temperature 37° C.—Standard dipping profile.

Sample 1: Size#2, natural, transparent, hard capsule shells—mono-, di-, and oligosaccharides amount 1.1% w/w—pullulan solution viscosity of 1470 mPa·s at 60° C.—gelling agent (carrageenan) 0.3% by weight over shell weight—co-gelling agent (KCl) 1.65% w/w by weight over shell weight;

Sample 2: Size#2, natural, transparent, hard capsule shells—mono-, di-, and oligosaccharides amount 2.4% w/w—pullulan solution viscosity of 1250 mPa·s at 60° C.—setting system as for Sample 1;

Sample 3 (comparative): Size#2, natural, transparent, standard NPcaps® capsules (from Capsugel, France) manufactured with commercial grade Pullulan PI-20—setting system as for Sample 1.

Brittleness of Samples 1-3 was tested by Tube Test after storage at different RH conditions:

|          | Broken capsules |        |        |
|----------|-----------------|--------|--------|
| Sample # | 14% RH          | 23% RH | 33% RH |
| 1        | 100             | 4      | 0      |
| 2        | 100             | 0      | 0      |
| 3 (comparative) | 100      | 70     | 14     |

Compared to standard NPcaps® capsules manufactured with commercial grade of Pullulan PI-20, a significant reduction of brittleness (level of broken capsules) was observed for storage under 33 & 23% RH.

Example 2

Sample 4 (comparative): Size#2, natural, transparent, pullulan capsules manufactured with commercial grade Pullulan PI-10—setting system as for Sample 1—manufacturing process as for Sample 1 but pullulan concentration in the aqueous composition was raised from 20% to 30% w/w.

Brittleness of Samples 3 and 4 (both comparative) was tested by Tube Test after storage at different shell moisture contents (obtained by storing shells at different RH conditions):

|          | % Broken capsules |        |        |
|----------|-------------------|--------|--------|
| Sample # | 12% moisture content | 10% moisture content | 8% moisture content |
| 3 (comparative) | 0 | 5 | 40 |
| 4 (comparative) | 0 | 20 | 60 |

Compared to standard NPcaps, capsules manufactured with pullulan PI-10 showed a significant increase in brittleness (level of broken capsules) when stored to achieve lower moisture contents. This example in combination with Example 1 shows that the level of mono-, di, and oligosaccharides in the pullulan is critical to obtain capsules with an improved brittleness whereas the average molecular weight of pullulan chains is not.

Example 3

Sample 5: natural, transparent, hard capsule shells—mono-, di-, and oligosaccharides amount 0.5% w/w—pullulan batch dimension is 400 Kg (industrial scale)—pullulan source is corn starch—manufacturing process and setting system as for Sample 1;

Sample 6: repeat of sample 6

Brittleness of Samples 3 and 5-6 was tested by Tube Test after storage at different RH conditions:

|          | % Broken capsules |        |        |
|----------|-------------------|--------|--------|
| Sample # | 14% RH            | 23% RH | 33% RH |
| 3 (comparative) | 100        | 70     | 14     |
| 5        | 100               | 18     | 0      |
| 6        | 100               | 10     | 0      |

Example 3 confirms reproducibility and repeatability of positive results with an industrial-scale batch of pullulan from corn starch on a pilot machine of conventional hard gelatin capsule production equipment.

Example 4

Hard capsule shells of Samples 7 and 8 were manufactured under standard production conditions i.e. with industrial full size hard capsules manufacturing machines following the general procedure disclosed in "Multiparticulate Oral Drug Delivery, edited by Isaac Ghebre-Sellassie Drugs and the Pharmaceutical Sciences Vol. 65 Marcel Dekker, Inc. 1994—Chapter 14, Capsule Shell composition and Manufacturing Ronnie Millender p. 357-383". The aqueous composition was optimized to the manufacture of pullulan capsules and consisted of:

Pullulan 22.5% by weight over weight of the composition,
Gelling agent (carrageenan) 0.067% by weight over weight of the composition
Co-gelling agent (KCl) 0.371% by weight over weight of the composition
Water to 100%

Sample 7: Capsule Lot#166181—Size #2, natural transparent hard capsule shells—mono-, di-, and oligosaccharides amount 0.5% w/w—pullulan source was non-GMO corn starch;

Sample 8 (comparative): Capsule Lot#165651—conventional NPcaps® manufactured using Pullulan PI-20 commercial grade Brittleness of Samples 7 and 8 was tested by Tube Test after storage at different RH conditions:

|          | % Broken capsules |        |        |
|----------|-------------------|--------|--------|
| Sample # | 11% RH            | 22% RH | 50% RH |
| 7        | 2                 | 0      | 0      |
| 8 (comparative) | 63         | 5      | 0      |

Despite the formulation optimization, the gap in terms of brittleness after storage at low RH between conventional pullulan grade capsules and the capsules of the present invention is remarkable.

Example 5

Sample 9: Capsule Lot#175451—Size #2, natural transparent hard capsule shells—mono-, di-, and oligosaccharides amount 0.5% w/w—pullulan source was tapioca starch—manufacturing process and setting system were as for Example 4;

Brittleness of Samples 7 and 9 was tested by Tube Test after storage at different RH conditions:

|  | % Broken capsules | | |
|---|---|---|---|
| Sample # | 11% RH | 22% RH | 50% RH |
| 7 | 2 | 0 | 0 |
| 9 | 5 | 0 | 0 |

Example 5 shows that pullulan capsules of the invention from Tapioca starch are equivalent in terms of mechanical properties under low moisture conditions to pullulan capsules of the invention from non-GMO corn starch.

Example 6

Sample 10: Lot#180531—Size #2, natural transparent hard capsule shells—mono-, di-, and oligosaccharides amount 0.9% w/w—pullulan batch #0A2921—pullulan source was tapioca starch—process conditions and setting system were as for Example 4;

Sample 11: Lot#180541—Size #2, white opaque body and cap pullulan hard capsule shells—mono-, di-, and oligosaccharides amount 0.9% w/w—pullulan batch #0A2921—pullulan source was tapioca starch—process conditions were as follows: TiO$_2$ was dispersed in an aqueous solution, then poured into a pullulan aqueous solution to obtain 2.0% w/w TiO$_2$ pigment content in the finished capsule. Capsule shells were manufactured according to the method and using the setting system described in Example 4;

Sample 12: Lot#180981—Size #2, natural transparent hard capsule shells—mono-, di-, and oligosaccharides amount 2.4% w/w—pullulan batch #0B0321—pullulan source was tapioca starch—process conditions and setting system were as for Example 4;

Sample 13: Lot#180521—Size #2, white opaque body and cap pullulan hard capsule shells—mono-, di-, and oligosaccharides amount 2.4% w/w—pullulan batch #0B0321—pullulan source was tapioca starch—process conditions and setting system were as for sample 11;

Brittleness of Samples 8-13 was tested by Tube Test after 1 week storage at 11% RH:

| Sample # | % Broken capsules |
|---|---|
| 9 | 8 |
| 10 | 10 |
| 11 | 33 |
| 12 | 15 |
| 13 | 55 |
| 8 (comparative) | 80 |

This example shows (i) a positive effect on capsule shell brittleness by reducing the content of mono-, di-, and oligosaccharides (ii) inclusion of TiO$_2$ as opacifier entails a slight worsening in shell brittleness. Thus, in case opaque capsules are desired, it is preferred to use low amounts of mono-, di-, and oligosaccharides amounts such as lower than about 1.0% w/w.

Example 7

Sample 14: Lot#179801—Size #2, natural transparent hard capsule shells—Conventional NPcaps® manufactured using commercial grade Pullulan PI-20—process conditions and setting system were as for Example 4;

3 batches (approximately 50 capsules, each) of natural, transparent pullulan capsules (one batch of Sample 9, one batch of Sample 10 and one batch of Sample 14) were filled with the following hygroscopic products:

Garlic Extract from Musyu-NinNiku powders PS-II Osada Co. LTD; initial powder moisture content: 1.3% w/w Bilberry extract from Bilbelon-25 from Tokiwa Phytochemical Co., LTD; initial powder moisture content: 1.8% w/w Garcinia extract from Garcitrin (Garcinol 0.5%) Sabinsa Japan Co., LTD; initial powder moisture content: 2.1% w/w After 1 week storage at room conditions (20° C., 50% RH) capsules moisture was controlled:

| | | Capsule LOD % after 1 week storage | | |
|---|---|---|---|---|
| Sample # | Capsule initial LOD % | Garlic | Bilberry | Garcinia |
| 9 | 11.6 | 6.5 | 7.1 | 6.7 |
| 10 | 11.4 | 6.3 | 6.8 | 6.8 |
| 14 (comparative) | 12.0 | 6.5 | 7.0 | 7.3 |

As predictable, moisture exchange between the hygroscopic fill and the capsule shell resulted in capsules dehydration. After moisture control, the filled capsules were tested according to the tube-test:

| | % Broken capsules | | |
|---|---|---|---|
| Sample # | Garlic | Bilberry | Garcinia |
| 9 | 0 | 0 | 0 |
| 10 | 0 | 0 | 0 |
| 14 (comparative) | 12 | 0 | 4 |

This example further confirms the advantage of the capsules of the present invention in terms of brittleness at an LOD of about 7%.

Example 8

Sample 15: Lot#93181—Size #2, white opaque body and cap pullulan hard capsule shells—Conventional NPcaps® manufactured using commercial grade Pullulan PI-20—process conditions and setting system were as for sample 11;

2 batches (approximately 50 capsules, each) of white opaque pullulan capsules (one batch of Sample 11 and one batch of Sample 15) were filled with Garlic and Garcinia extracts (see Example 7 for details):

After 1 week storage at room conditions (20° C., 50% RH) capsules were tested with tube test:

|          | % Broken capsules | |
| Sample # | Garlic | Garcinia |
| --- | --- | --- |
| 11 | 4 | 0 |
| 15 (comparative) | 80 | 8 |

A significant improvement in terms of brittleness between standard commercial pullulan capsules and the capsules of the present invention is apparent.

Example 9

Capsule smell was measured by a group of 5 panellists on capsules from Sample 7 and Sample 8:

| | Score for each panellist # | | | | | | | |
| Sample # | #1 | #2 | #3 | #4 | #5 | Avg. | Dev. | Tot. |
| --- | --- | --- | --- | --- | --- | --- | --- | --- |
| 7 | 3 | 3 | 3 | 3 | 3 | 3 | 0 | 15 |
| 8 (comparative) | 3 | 3 | 2 | 3 | 3 | 2.8 | 0.4 | 14 |

No significant difference of smell was detected between pullulan capsules of the invention and NPcaps pullulan commercial capsules.

Example 10

Following the test procedure disclosed in the present application, compatibility with CFM (capsule filling machines) was evaluated for capsule from samples 7 and 8:

| Sample # | Capsules cracking – Capsule batch = 1000 capsules | Non separation at 10 cm Hg – Capsule batch = 1500 capsules |
| --- | --- | --- |
| 7 | 0 | 0 |
| 8 (comparative) | 0 | 0 |

This example shows that shell compatibility with modern filling machines is substantially identical for the hard capsule shells of the present invention and conventional pullulan hard capsule shells.

The invention claimed is:

1. A hard capsule shell comprising a setting system, and at least one pullulan, wherein the pullulan is substantially free of mono-, di-, and oligosaccharides, wherein the amount of mono-, di-, and oligosaccharides in the pullulan is less than 2.5% by weight of pullulan on a dry solid basis, and wherein the shell comprises between 65% and 99% of the pullulan by weight of the shell.

2. The hard capsule shell according to claim 1, wherein the pullulan has an average molecular weight ranging from about 100 KDa to about 400 KDa.

3. The hard capsule shell according to claim 1, wherein the pullulan has a melt viscosity at about 60° C. ranging from about 500 cPs to about 1500 cPs.

4. The hard capsule shell according to claim 1, wherein the pullulan comprises less than about 1.0% of mono-, di- and oligosaccharides by weight of pullulan, on a dry solid basis.

5. The hard capsule shell according to claim 1, wherein the pullulan is produced from corn or tapioca starch.

6. The hard capsule shell according to claim 1, further comprising at least one ingredient selected from the group consisting of pharmaceutically or food acceptable dyes and/or colouring agents, pharmaceutically or food acceptable sequestering agents, pharmaceutically or food acceptable plasticisers, pharmaceutically or food acceptable sweeteners and/or flavouring agents, pharmaceutically or food acceptable surfactants, and mixtures thereof.

7. A hard capsule comprising the hard capsule shell according to claim 1 filled with one or more substances, wherein at least one substance is in solid, semi-solid and/or liquid form.

8. The hard capsule shell according to claim 1, wherein the shell has a shell thickness less than about 500 μm.

9. The hard capsule shell according to claim 8, wherein the shell has a shell thickness less than about 250 μm.

10. The hard capsule shell according to claim 1, wherein the pullulan comprises less than about 0.7% of mono-, di-, and oligosaccharides by weight of pullulan, on a dry solid basis.

11. The hard capsule shell according to claim 1, wherein the pullulan comprises less than about 0.6% of mono-, di-, and oligosaccharides by weight of pullulan, on a dry solid basis.

\* \* \* \* \*